United States Patent
Amouzegar et al.

(10) Patent No.: US 8,350,089 B2
(45) Date of Patent: Jan. 8, 2013

(54) YIELD-EFFICIENT PROCESS FOR THE PRODUCTION OF HIGHLY PURE 2-METHYL-1,4-NAPHTHOQUINONE AND ITS DERIVATIVES

(75) Inventors: Kamyab Amouzegar, Mount-Royal (CA); Behzad Mahdavi, Saint-Jean des Piles (CA); Charles Didier, Visp (CH); Alexander Lieb, Brig (CH); Mathieu Langevin, St-Boniface (CA)

(73) Assignee: Lonza Ltd., Basel (CH)

( * ) Notice: Subject to any disclaimer, the term of this patent is extended or adjusted under 35 U.S.C. 154(b) by 92 days.

(21) Appl. No.: 13/004,629

(22) Filed: Jan. 11, 2011

(65) Prior Publication Data

US 2011/0263904 A1    Oct. 27, 2011

Related U.S. Application Data

(60) Provisional application No. 61/294,694, filed on Jan. 13, 2010.

(30) Foreign Application Priority Data

Jan. 13, 2010 (EP) .................................. 10000252

(51) Int. Cl.
*C07C 45/00* (2006.01)
*C07C 50/18* (2006.01)
(52) U.S. Cl. ......... 568/309; 568/317; 552/208; 552/292
(58) Field of Classification Search .................. 568/309, 568/317; 552/208, 292
See application file for complete search history.

(56) References Cited

U.S. PATENT DOCUMENTS

| | | |
|---|---|---|
| 3,751,437 A | 8/1973 | Huba |
| 5,329,026 A | 7/1994 | Sugishima et al. |
| 5,770,774 A | 6/1998 | Joo et al. |

FOREIGN PATENT DOCUMENTS

| | | |
|---|---|---|
| IN | 157224 A1 | 2/1986 |
| JP | 60252445 A | 12/1985 |

OTHER PUBLICATIONS

Song et al., "Process Improvement on Synthesis of 2-methyl-1,4-naphthoquinone", Chemical Reaction Engineering and Technology, vol. 23, No. 4, pp. 380-384; 2007.
Jacek Skarzewski, "Cerium Catalyzed Persulfate Oxidation of Polycyclic Aromatic Hydrocarbons to Quinones", Tetrahedron, vol. 40, No. 23, pp. 4997-5000; 1984.
Adam et al., "Homogeneous Catalytic Oxidation of Arenes and a New Synthesis of Vitamin K3", Angew. Chem. Int. Ed. Engl., vol. 33, No. 23/24, pp. 2475-2477; 1994.

*Primary Examiner* — Sikarl Witherspoon
(74) *Attorney, Agent, or Firm* — Hoffmann & Baron, LLP

(57) ABSTRACT

The present invention discloses a process for the production of 2-methyl-1,4-naphthoquinone and its bisulfite adducts, comprising the following steps:
a) oxidizing 2-methyl-naphthalene (2-MNA) to achieve an organic phase containing 2-methyl-naphthoquinone (2-MNQ) and 6-methyl-naphthoquinone (6-MNQ);
b) subjecting said organic phase to treatment with an aqueous solution of a bisulfite salt to extract preferentially the 6-MNQ isomer from the organic phase;
c) separating said organic phase from the aqueous phase;
d) subjecting the organic phase of process step c) to a second bisulfidation step with an aqueous solution of a bisulfite salt, resulting in an organic phase containing 2-MNA and trace amounts of 2-MNQ and an aqueous phase containing 2-MSB and trace amounts of 6-MSB;
e) optionally removing interfering bisulfite ions from the aqueous phase of process step c);
f) raising the pH of the aqueous phase from step c) or e) to higher than 8.5 in the presence of a solvent resulting in an organic phase containing 2-MNQ;
g) combining the organic phase from step f) with the organic phase being treated in the process step d);
h) recycling the organic phase from step d) back to step a) to be used as solvent for the oxidation reaction of 2-MNA.

17 Claims, 2 Drawing Sheets

YIELD-EFFICIENT PROCESS FOR THE PRODUCTION OF HIGHLY PURE 2-METHYL-1,4-NAPHTHOQUINONE AND ITS DERIVATIVES

CROSS-REFERENCE TO RELATED APPLICATION

Applicants claim the benefit of priority from U.S. Provisional Patent Application No. 61/294,694 and European Patent Application No. 10000252.6, both of which were filed Jan. 13, 2010; and the disclosure of each is incorporated herein by reference.

The present invention discloses a method for the preparation of high purity 2-methyl-1,4-naphthoquinone (Menadione, 2 isomer) and its derivatives, in which the 6-methyl-1,4-naphthoquinone isomer (6 isomer) formed as a byproduct during the 2-methyl-naphthalene oxidation is extracted selectively as a bisulfite adduct. The bisulfite solution is then treated in a recovery step (involving a β-cleavage reaction to form pure Menadione) which allows minimizing the Menadione losses due to the bisulfite solution treatment.

BACKGROUND OF THE INVENTION

Several processes for producing Menadione are known in the art.

One common technique is the oxidation of 2-methyl-naphthalene by using sodium dichromate in aqueous sulfuric acid solution. In this case, despite the low selectivity for the 2-isomer, the high degree of destruction of the 6-isomer due to the added excess hexavalent chromium results in a final product containing a high content of Menadione. For example, the U.S. Pat. No. 3,751,437 discloses that although the reaction selectivity for the 2-methyl-1,4-naphthoquinone is not very high (50-53%), the final product is mainly composed of Menadione (94-97%), some unreacted 2-methyl-naphthalene (2-MNA) and small amounts of undefined impurities. The main drawbacks of this process are the very low selectivity of the reaction for the formation of the 2-methyl-1,4-naphthoquinone isomer, the need for excessive amounts of highly toxic hexavalent chromium as oxidizing agent and the creation of significant amounts of basic chromium sulfate as the reaction byproduct.

In order to resolve these problems related to the process described above, the use of other oxidizing agents has been proposed in the state of the art. However, in all the proposed alternatives using other oxidizing agents, the 6 isomer is present in the final product mixture at much higher ratios. For example, when hydrogen peroxide (in the presence of a methyltrioxorhenium catalyst) is used to oxidize 2-MNA, the final methyl-quinones are composed of 86% of 2 isomer and 14% of 6 isomer i.e. a ratio of 2 to 6 isomer of 7:1 (W. Adam, W. A. Herrmann J. Lin, C. R. Saha-Moeller, R. W. Fischer and J. D. G. Correia, <<Homogeneous catalytic oxidation of arenes and a new synthesis of vitamin K3, Angew. Chem. Int. Ed. Engl., 33, p. 2475-2477 (1994)). In another example, when 2-MNA is oxidized using ammonium persulfate (in the presence of catalytic amounts of cerium ammonium sulfate and silver nitrate), the ratio of the 2 to 6 isomer was around 3:1 (J. Skarzewski, <<Cerium catalyzed persulfate oxidation of polycyclic aromatic hydrocarbons to quinones, Tetrahedron, 40, p 4997-5000 (1984)). The use of ceric sulfate as oxidant in an acetonitrile-sulfuric acid mixture also resulted in relatively high amounts of 6 isomer in the final product, i.e. 2 to 6 isomer ratio of 6.5:1 (IN 157224 A).

While the use of highly toxic hexavalent chromium as well as the creation of a considerable amount of the basic chromium sulfate is avoided in the methods of the state of the art cited above, the final reaction mixture contains significant amounts of the 6 isomer which is quite difficult to separate from the desired 2 isomer due to the similar properties of the two isomers. There are different proposals in the art to separate the two isomers. The most relevant strategies are:

- Avoiding the creation of the 6 isomer by using a different raw material and a Diels-Alder reaction
- Separating the undesired 6 isomer by its selective transformation in methyl-anthraquinone
- Treating the final product mixture with an aqueous bisulfite solution to separate the 6 isomer However, all of these strategies suffer from major disadvantages:

The U.S. Pat. No. 5,770,774 proposes to avoid making the 6-isomer by using 2-methyl-1,4-benzoquinone as raw material. This product is reacted with 1,3-butadiene in a Diels-Alder reaction to make 2-methyl-4-a,5,8,8a-tetrahydro-1,4-naphthoquinone, which is then oxidized to 2-methyl-1,4-naphthoquinone.

There are several problems associated with this procedure. For one, the raw material 2-methyl-1,4-benzoquinone is expensive and not readily available in large amounts. Furthermore, 1,3-butadiene is a highly toxic agent. Finally, the reaction presupposes the presence of a Lewis acid catalyst in order to proceed.

The U.S. Pat. No. 5,329,026 discloses the reaction of 6-methyl-1,4-naphthoquinone with 1,3-butadiene to make 1,4,4a,9a-tetrahydro-6-methylanthraquinone. The latter molecule can then be oxidized to the methyl-anthraquinone by adding sodium hydroxide and bubbling air as oxidation agent. The 2-methyl-1,4-naphthoquinone isomer hardly undergoes the same Diels-Alder reaction with the 1,3-butadiene due to the steric hindrance and difference in electron density.

In addition to the problems of the previous process (use of highly toxic 1,3-butadiene), there are further disadvantages associated with this process: it has to be conducted at high temperatures (ca. 120° C.) and high reaction pressure, thus necessitating the use of expensive apparatuses like autoclaves with a high energy consumption. Furthermore, the reaction time is very long (up to 4 hours).

The Japanese Application 60252445 A discloses the treatment of the final product mixture with an aqueous bisulfite solution to separate the 6-isomer. The organic solvent containing the starting and the final products of the 2-MNA oxidation reaction is first cooled down to precipitate part of the 2-MNQ formed during the oxidation. The remaining solvent phase is then treated with a bisulfite solution to extract most of the 6 isomer as well as part of the 2-isomer as bisulfite adduct that is soluble in the aqueous phase. Due to the fact that the 6-isomer reacts much faster than the 2-isomer, the remaining solvent phase presents a much higher ratio of 2- to 6-isomer. The organic phase is cooled down to obtain 2-MNQ crystals (94% purity). The solvent filtrate is treated in a selective bisulfidation step in which typically 25-30% of 2-MNQ is extracted in order to reach around 90% 6-MNQ extraction rates (this represents around 8 to 10% of the total 2-MNQ produced during the oxidation step). The aqueous solution containing bisulfite adducts of 2-MNQ and 6-MNQ becomes a waste.

The 2-MNQ crystals from the first crystallization are dissolved in the organic phase and recrystallized (around 65% precipitation yield). The 2-MNQ produced contains still on average 2% of the 6-MNQ isomer. The aqueous phase of the oxidation step is extracted in an extraction step using extra solvent that is then combined with the solvent from the second crystallization step. The obtained mixture needs to go through an additional step of solvent evaporation in order to concentrate the organic phase before its use in the next oxidation cycle. The overall process is presented in FIG. 1.

There are various drawbacks associated with the process as described above.

Firstly, significant amounts of 2-MNQ (around 8% in first cycle of example 3 and around 10% overall assuming a yield of 2-MNQ crystals of 55% and the assumed 65% overall yield for a cerium sulfate process) are lost in the bisulfidation step and not recovered.

Second, the produced 2-MNQ is not of a very high purity after the first crystallization due to the fact that the selective bisulfidation is not carried out before this crystallization. The purity of 2-MNQ even after the second (final) crystallization is less than 98% due to the fact that 10% of the original 6-MNQ is still left in the solvent after the selective bisulfidation (a higher extraction rate results in excessively high 2-MNQ extraction and loss rates).

Third, an important part of the produced 2-MNQ is recycled back to the oxidation reactor (around 35% in the example 3) which may result in overoxidation and further losses of 2-MNQ.

Fourth, the organic phase of the extraction of the aqueous phase from the oxidation step is mixed with the filtrate from step 4 (after the second crystallization) and before it gets recycled it needs to be concentrated by evaporation. This adds additional steps and costs to the process.

Chengying et al later proposed an approach similar to the Japanese patent based on using 2-MNQ precipitation, followed by bisulfidation reaction and finally the re-dissolution of the precipitated 2-MNQ in the initial solvent phase to separate the 6 isomer from the 2 isomer (<<Process improvement on synthesis of 2-methyl-1,4-naphthoquinone>>, Song Chengying, Wang Liucheng, Zhao Jianhong and Xu Haisheng, Chemical Reaction Engineering and Technology, vol. 23, No. 4, Aug. 2007). Contrary to the Japanese patent approach, the ratio of 2-MNQ to solvent proposed by these authors seems very low (a weight ratio of solvent to 2-MNQ of 4 compared to between 12 and 120 in the case of the Japanese patent). At this ratio, around 95% of the 2-MNQ formed will precipitate at the first crystallization step. However, this will be accompanied also by a high rate of 6-MNQ precipitation resulting in a low purity of the first 2-MNQ crystals. Therefore, despite high extraction rates of dissolved 6-MNQ at the bisulfidation step, once the first 2-MNQ crystals are re-dissolved in the solvent phase after the selective bisulfidation step, the residual 6-MNQ in the final 2-MNQ obtained in the second crystallization step should be significantly higher than the 0.5% claimed by the authors resulting in a relatively low purity of final 2-MNQ product.

Problem Underlying the Invention

The technical problem to be solved is to devise a method for producing Menadione and Menadione derivatives which overcomes the disadvantages of the processes disclosed in the state of the art.

Specifically, the process to produce Menadione and Menadione derivatives shall avoid the use of aggressive oxidizing agents like hexavalent chromium, without compromising the purity of the Menadione or its derivatives.

Furthermore, the envisaged process shall avoid the application of high temperatures and pressures as well as toxic reagents.

Finally, the envisaged process shall achieve a selectivity, yield and purity that is at least comparable, if not better than what is currently known in the art.

DESCRIPTION OF THE INVENTION

The technical problem outlined above is surprisingly solved by a process to produce Menadione and its derivatives as disclosed in the claims.

Specifically, the method according to the invention is based on treating the organic phase from the oxidation step of 2-MNA with an aqueous solution of a bisulfite salt in such a manner that the 6-MNQ isomer is reacted with a higher selectivity than that of 2-MNQ. The organic phase after the selective bisulfidation step (SB), is then sent to another bisulfidation step in which most of the remaining 2-MNQ and 6-MNQ are extracted as bisulfite adducts in the aqueous bisulfite solution. The final organic phase containing very small residual amounts of 2-MNQ is enriched in 2-MNA and recycled back to the oxidation step. The aqueous phase from the SB step is then sent to a recovery step in which (if necessary) the interfering bisulfite ions are removed from the solution and the pH is increased to more than 8.5, more preferably to between 10 and 12 and most preferably between 11 and 12 in the presence of the organic phase (preferably from the non selective bisulfidation step). In an alternative embodiment, the increase in pH is carried out in the absence of a solvent and the precipitated 2-MNQ may then be recovered as a solid by a liquid-solid separation method such as filtration. The organic phase from the recovery step may be cooled down to precipitate very pure 2-MNQ solid that may be separated by any solid-liquid separation method. The obtained 2-MNQ presents a very high purity in terms of absence of the 6-MNQ isomer due to the fact that the bisulfite adduct of the 6-MNQ isomer hardly undergoes the β-cleavage reaction during the recovery step. The remaining organic phase may be sent to the non selective bisulfidation step to convert most of the residual 2-MNQ into 2-MNQ bisulfite adduct along with the solvent phase from the SB step and be recycled to the oxidation step as mentioned before. The bisulfite adduct of 2-MNQ contained in the aqueous phase from the non selective bisulfidation step may be precipitated by known methods (e.g. cooling, salt addition, solvent addition, etc) and dried to obtain the solid form of the bisulfite adduct of Menadione. Alternatively, it may be used to form other derivatives of vitamin K3 such as MNB, MPB, etc, at a high yield and high purity.

The residual amount of 2-MNQ contained in the spent oxidant solution after the 2-MNA oxidation step may be extracted using the solvent from the non selective bisulfidation step before its recycling to the oxidation step.

Figure 1:
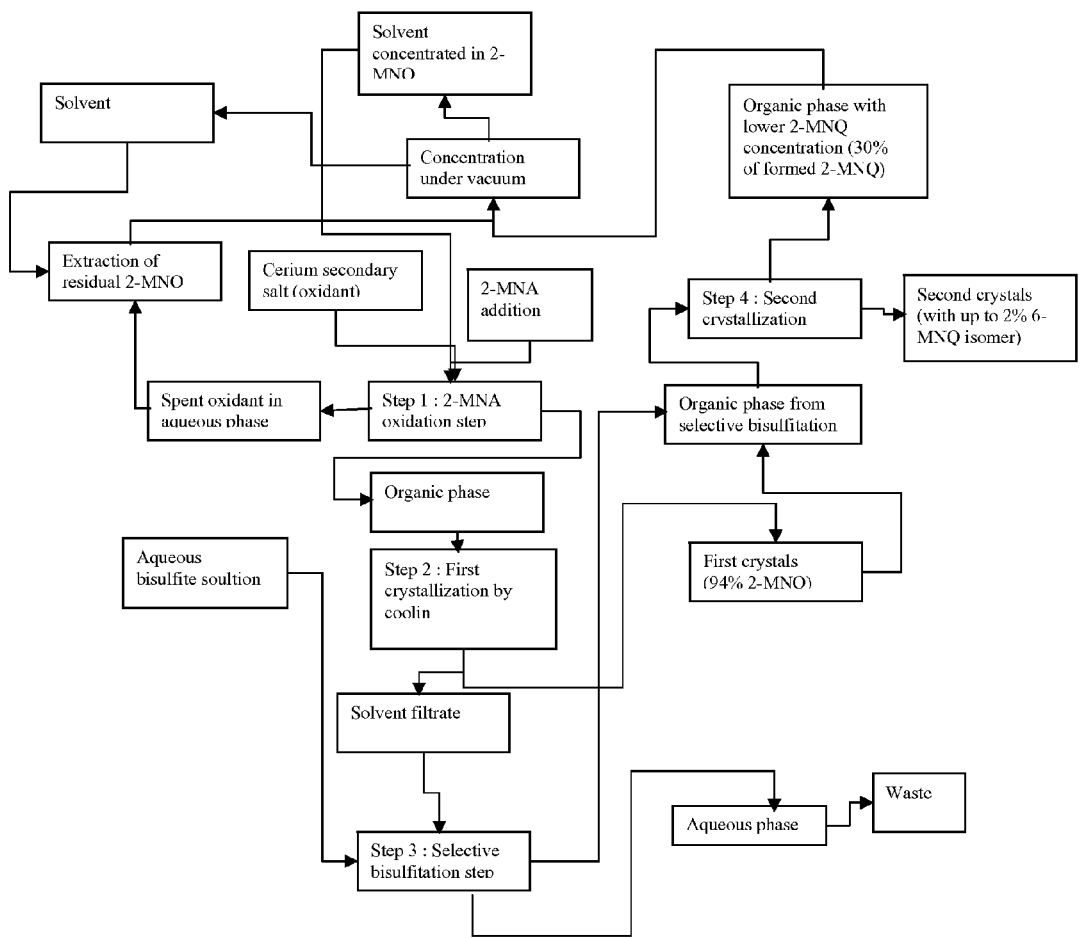
FIG. 1 is a diagram of the process according to JP 60-252445 A.
Figure 2:
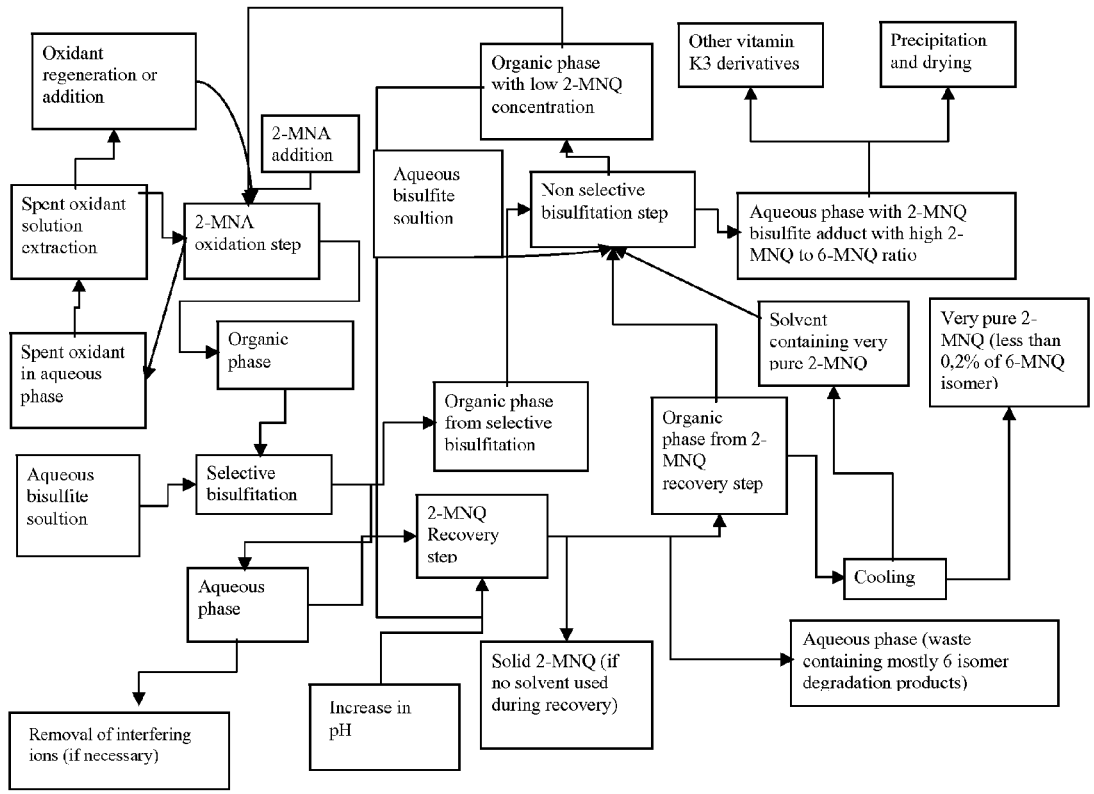
FIG. 2 is a diagram of the process according to the invention.

FIG. 2 shows the different steps involved in the method according to the invention.

The solid Menadione obtained from the recovery step preferably contains less than 0.5% w/w % of the 6-MNQ isomer, more preferably 0.2% and most preferably less than 0.1%, which is considerably less than the typical 2% content reported in the state of the art, e.g. the Japanese patent 60-252445. The preferred 2-MNQ recovery yields according to the invention are around 90%, more preferably 92% and most preferably 95%. Furthermore, with an extraction rate during SB step of preferably 30%, more preferably 28% and most preferably 25% of the 2-MNQ produced during the oxidation step, the total loss of 2-MNQ due to SB and recovery step combined would be around 1.5% to 3% which is again considerably lower than the 8% to 10% losses observed when selective bisulfidation is used without combination with the recovery step (e.g. Japanese patent 60-252445).

The 2-MNA oxidation step preferably takes place at a temperature in the range of 0 to 100° C., more preferably 25-60° C. and most preferably 25-40° C.

The 2-MNA oxidation step according to the invention can be executed using any suitable oxidizing agent known in the art. However, it may be preferred that said oxidizing agent is selected from the group consisting of a Ce(III)/Ce(IV) salt redox couple.

The selective bisulfidation step according to the invention may be carried out at a temperature in the range of 0-70° C., more preferably 10-50° C. and most preferably 25-40° C. Any bisulfite salt capable of dissolving in water may be used as a bisulfidation agent. However, it may be preferred that the bisulfite salt is selected from the group consisting of sodium or potassium bisulfite. Preferably, the bisulfite solution according to the invention has a concentration of 0.1 to 4 M, more preferably 0.5 to 2 M and most preferably 0.5 M.

The non-selective bisulfidation step according to the invention may be carried out at a temperature in the range of 0-70° C., more preferably 10-50° C. and most preferably 25-40° C. Any bisulfite salt may be used as a bisulfidation agent. However, it may be preferred that the bisulfite salt is selected from the group consisting of sodium or potassium bisulfite.

It has also been observed that the selectivity of the selective bisulfidation varies according to the agitation conditions. As the agitation is increased, a higher extraction yield of 6-MNQ may be obtained at a lower 2-MNQ extraction rate, which also minimizes the losses of 2-MNQ as it may be seen from examples 1 to 3. Thus, it may be preferred that the selective bisulfidation takes place under agitation. However, the agitation should not be too vigorous as to result in the formation of a stable emulsion between the organic phase and the aqueous bisulfite solution. The determination of the precise agitation conditions is within the routine capability of the skilled person.

Also the other derivatives of vitamin K3 produced from the current proposed method show an important improvement in the quality of the final product. For example, MNB produced using the proposed process contains no detectable amounts of the 6 isomer derivative, whereas without the SB step, the final MNB contains typically between 0.1% and 1% of the 6 isomer derivative. Also, the application of this approach allows maximizing the precipitation yield of the vitamin K3 derivatives, as the very low concentration of the 6 isomer bisulfite adduct allows maximizing the precipitation rate of the 2 isomer adduct or its derivatives without provoking the precipitation of the 6 isomer adduct derivatives which would result in a less pure vitamin K3 derivative.

The present invention contemplates the production of Menadione and its derivatives. It may be especially preferred that said derivatives are selected from the group consisting of Menadione bisulfite adducts that may be isolated as organic salts containing an inorganic cation such as sodium (MSB) or potassium or an organic cation as protonated forms of compounds such as Nicotinamide (MNB), dimethylPyrimidinol (MPB), p-Amino-Benzoic acid, etc.

In summary, the present invention has several advantages compared to the prior art:

In comparison to the methods according to the state of the art, the use of oxidizing agents other than hexavalent chromium or an excess amount of it becomes possible without compromising the purity of the vitamin K3 or its derivatives produced.

In comparison to the methods in the art which propose the use of Diels-Alder reactions, the application of high temperatures, high pressures and highly toxic reagents is avoided.

Specifically in comparison with the approach according to the Japanese patent 60-252445, the following improvements have been achieved:

The total loss of 2-MNQ due to the combined SB-Recovery steps is between 1.5% and 3%, compared to 8% to 10% for the Japanese patent.

The residual concentration of the 6-MNQ isomer in the isolated 2-MNQ solid is less than 0.2% compared to the typical average of 2% reported in the Japanese patent.

The use of higher agitation conditions also results in improved selectivities.

The need for the evaporation step of the combined organic phases of the extraction of the aqueous phase (from the oxidation step) and the filtrate from crystallization step is avoided by doing a second bisulfidation and by using the final organic phase for the extraction of the aqueous phase of the oxidation step.

A very small fraction of the formed 2-MNQ is recycled back to the oxidation step which minimizes additional losses due to overoxidation of already formed 2-MNQ (less than 2% of 2-MNQ is sent back to oxidation step compared to up to 30% in the Japanese patent).

The process according to the invention will be further explained in the following, non-limiting examples.

EXAMPLE 1

380 ml of a sodium bisulfite solution having a bisulfite concentration of 0.5 M were transferred to a 2 liter reactor containing 1580 ml of a water immiscible aliphatic solvent containing 0.0214 M of 2-MNQ and 0.0042 M of 6-MNQ. The reactor was equipped with a conventional 4 blade propeller and the agitation speed was set to 400 rpm. Samples of the organic phase were taken and analyzed by GC to determine the residual concentration of the 2 and 6 MNQ isomers. The results are presented in table 1 below:

TABLE 1

| Bisulfidation Time (sec) | 2-MNQ in solvent (M) | Extracted 2-MNQ fraction | 6-MNQ in solvent (M) | Extracted 6-MNQ fraction | 2-MNQ to 6-MNQ ratio in solvent | % of 2 isomer in the total methyl-1,4-naphthoquinone in solvent |
|---|---|---|---|---|---|---|
| 0 | 0.0214 | 0% | 0.0042 | 0% | 5.1 | 84% |
| 60 | 0.0213 | 1% | 0.0035 | 16% | 6.0 | 86% |
| 120 | 0.0211 | 2% | 0.0029 | 31% | 7.2 | 88% |
| 180 | 0.0195 | 9% | 0.0023 | 45% | 8.4 | 89% |
| 300 | 0.0188 | 12% | 0.0017 | 59% | 10.8 | 92% |

TABLE 1-continued

| Bisulfidation Time (sec) | 2-MNQ in solvent (M) | Extracted 2-MNQ fraction | 6-MNQ in solvent (M) | Extracted 6-MNQ fraction | 2-MNQ to 6-MNQ ratio in solvent | % of 2 isomer in the total methyl-1,4-naphthoquinone in solvent |
|---|---|---|---|---|---|---|
| 660  | 0.0164 | 24% | 0.0009 | 79% | 18.6 | 95% |
| 900  | 0.0150 | 30% | 0.0007 | 85% | 23.0 | 96% |
| 1800 | 0.0119 | 45% | 0.0004 | 90% | 29.3 | 97% |

As it may be seen, after 30 minutes of reaction, the 2 to 6 isomer ratio in the organic phase has increased from the original value of 5.1 to more than 29 (around 97% of the 1,4-methyl-naphthoquinone in the solvent is the 2 isomer).

EXAMPLE 2

400 ml of a sodium bisulfite solution having a bisulfite concentration of 0.5 M were transferred to a 2 liter reactor containing 1600 ml of a water immiscible aliphatic solvent containing 0.0247 M of 2-MNQ and 0.0052 M of 6-MNQ. The reactor was equipped with a conventional 4 blade propeller. In order to improve the agitation conditions compared to those used in the prior example, two baffles were installed in the reactor and the agitation speed was set to 500 rpm. Samples of the organic phase were taken and analyzed by GC to determine the residual concentration of the 2 and 6 MNQ isomers. The results are presented in table 2 below:

TABLE 2

| Bisulfidation Time (sec) | 2-MNQ in solvent (M) | Extracted 2-MNQ fraction | 6-MNQ in solvent (M) | Extracted 6-MNQ fraction | 2-MNQ to 6-MNQ ratio in solvent | % of 2 isomer in the total methyl-1,4-naphthoquinone in solvent |
|---|---|---|---|---|---|---|
| 0    | 0.0247 | 0%  | 0.0052 | 0%  | 4.8  | 83% |
| 120  | 0.0235 | 5%  | 0.0039 | 25% | 6.1  | 86% |
| 300  | 0.0220 | 11% | 0.0024 | 53% | 9.0  | 90% |
| 600  | 0.0199 | 20% | 0.0010 | 81% | 20.2 | 95% |
| 780  | 0.0184 | 26% | 0.0007 | 87% | 28.2 | 97% |
| 1080 | 0.0158 | 36% | 0.0004 | 92% | 38.8 | 97% |
| 1200 | 0.0145 | 41% | 0.0004 | 93% | 39.1 | 98% |
| 1500 | 0.0135 | 45% | 0.0004 | 93% | 38.0 | 97% |
| 1800 | 0.0115 | 53% | 0.0003 | 93% | 33.8 | 97% |

It may be seen that the more vigorous agitation results in a better selectivity for 6 isomer extraction. In fact compared to example 1, to reach an organic phase containing 97% of the 2 isomer, only 26% of the 2-MNQ contained in the original solvent was extracted (compared to around 45% for the agitation conditions of example 1). Also the higher agitation allows to reach the 97% content in the solvent in a much shorter time (13 minutes compared to 30 minutes in example 1).

It is also important to see that the residence time has also an effect on the selectivity since after certain period, the purity does not improve but the fraction of extracted 2-MNQ increases.

EXAMPLE 3

750 ml of a sodium bisulfite solution having a bisulfite concentration of 0.5 M were transferred to a 4 liter reactor containing 3000 ml of a water immiscible aliphatic solvent containing 0.0229 M of 2-MNQ and 0.0042 M of 6-MNQ. The reactor was equipped with a Silverstone propeller instead of the conventional agitation propellers used in examples 1 and 2. The agitation speed was 3400 rpm. Samples of the organic phase were taken and analyzed by GC to determine the residual concentration of the 2 and 6 MNQ isomers. The results are presented in table 3 below:

TABLE 3

| Bisulfidation Time (sec) | 2-MNQ in solvent (M) | Extracted 2-MNQ fraction | 6-MNQ in solvent (M) | Extracted 6-MNQ fraction | 2-MNQ to 6-MNQ ratio in solvent | % of 2 isomer in the total methyl-1,4-naphthoquinone in solvent |
|---|---|---|---|---|---|---|
| 0   | 0.0229 | 0%  | 0.0042 | 0%  | 5.5  | 85% |
| 60  | 0.0220 | 4%  | 0.0030 | 28% | 7.3  | 88% |
| 180 | 0.0211 | 8%  | 0.0024 | 43% | 8.9  | 90% |
| 300 | 0.0205 | 10% | 0.0016 | 62% | 12.9 | 93% |
| 420 | 0.0191 | 16% | 0.0010 | 77% | 19.9 | 95% |
| 540 | 0.0184 | 19% | 0.0007 | 82% | 25.1 | 96% |
| 600 | 0.0182 | 20% | 0.0006 | 84% | 28.2 | 97% |
| 720 | 0.0177 | 23% | 0.0005 | 88% | 34.3 | 97% |

It may be seen that the more vigorous agitation results in even higher selectivity for 6 isomer extraction. In fact compared to example 1, to reach an organic phase containing 97% of the 2 isomer, only 20% of the 2-MNQ contained in the original solvent was extracted (compared to around 45% for the agitation conditions of example 1 and 26% for example 2). Also the higher agitation again allows to reach the 97% content in the solvent in a much shorter time (10 minutes compared to 30 minutes in example 1 and 13 minutes for example 2).

EXAMPLE 4

An organic phase containing 430 parts of 2-MNA, 65 parts of 2-MNQ and 14 parts of 6-MNQ was oxidized in a continuous mode by a ceric and cerous methanesulfonate aqueous mixture. The organic phase at the oxidation step outlet contained 17 parts of 2-MNA, 275 parts of 2-MNQ and 56 parts of 6-MNQ. The organic phase was then put in contact with a sodium bisulfite solution to form the bisulfite adduct of both isomers. The organic phase at the bisulfidation reactor outlet contained 28 parts of 2-MNQ and 4 parts of 6-MNQ representing 90% and 94% of extraction during bisulfidation for the 2 and 6 isomers, respectively. The analysis of the final aqueous phase showed a concentration of 0.92 M for the 2-MSB and 0.19 M for the 6-MSB adducts. The aqueous phase was then mixed in equimolar ratio with a solution of nicotinamide in water and then concentrated sulfuric acid was added gradually over a period of 150 minutes. Starting from the end of the sulfuric acid addition, samples of the solid MNB were taken from the suspension and washed with water and analyzed for the presence of the 6 isomer of the Methyl-naphthoquinone Nicotinamide Bisulfite (6-MNB). As it may be seen from table 4 below, the concentration of the 6-MNB starts to increase after 4 hours of elapsed time between the end of acid addition and the solid filtration to reach up to 0.72% and even 2.74% after 5 hours.

TABLE 4

| Waiting time before filtration (min.) | 6-MNB in final MNB solid (%) |
| --- | --- |
| 5 | 0.13% |
| 65 | 0.20% |
| 125 | 0.16% |
| 185 | 0.18% |
| 245 | 1.15% |
| 305 | 2.74% |

EXAMPLE 5

2-MNA was oxidized in the same manner as described in example 4. However, in this case the organic phase was reacted continuously with an aqueous solution of sodium bisulfite in a selective bisulfidation reactor in which the residence time and agitation conditions were set so that 78-79% of the 6-MNQ and only 25-28% of the 2-MNQ were extracted from the organic phase as their bisulfite adduct. Once the concentration of residual sodium bisulfite reached 0.5 M, fresh concentrated sodium bisulfite solution was added to the selective bisulfidation and equivalent volumes of the aqueous phase were removed from the reactor so that the concentration of all species in the aqueous phase remained practically constant. Table 5 below shows the concentration of adducts of the 2 and 6 isomers in the removed aqueous phase.

TABLE 5

| Component | 2-MSB (M) | 6-MSB (M) |
| --- | --- | --- |
| Concentration | 0.833 | 0.315 |

During the continuous operation of the selective bisulfidation reactor, 4 samples of the organic phase were taken and reacted with the same sodium bisulfite solution in a consecutive way in order to increase the concentration of the residual 2-MSB and therefore mimic a continuous bisulfidation reaction. The results in terms of 2-MNQ and 6-MNQ concentrations in the initial and final solvent phase as well as the concentration of the 2-MSB and 6-MSB in the aqueous bisulfite solution are presented in table 6 below.

TABLE 6

| Bisulfidation cycle | 2-MNQ in initial solvent (M) | 6-MNQ in initial solvent (M) | 2-MNQ in final solvent (M) | 6-MNQ in final solvent (M) | 2-MSB (M) | 6-MSB (M) |
| --- | --- | --- | --- | --- | --- | --- |
| 1 | 0.0149 | 0.0006 | 0.0001 | 0.0000 | 0.232 | 0.0008 |
| 2 | 0.0054 | 0.0005 | 0.0006 | 0.0000 | 0.3398 | 0.0018 |
| 3 | 0.0054 | 0.0005 | 0.0021 | 0.0000 | 0.4084 | 0.0023 |
| 4 | 0.0054 | 0.0005 | 0.0010 | 0.0000 | 0.499 | 0.0024 |

100 parts of the final aqueous bisulfite solution containing 0.499 M of 2-MSB and 0.0024 M of 6-MSB were then used to prepare MNB by addition of an aqueous solution containing 15 parts of water and 6 parts of nicotinamide. 4.13 parts of sulfuric acid 93% were added gradually to the mixture over a period of 30 minutes. After a waiting period of 60 minutes, the precipitated MNB was filtered and washed with water and the solid MNB was then dried and analyzed for the presence of 6-MNB impurity. The concentration of the residual 2-MSB reached 0.07 M corresponding to 83% of precipitation efficiency. In another experiment, the MNB precipitation was performed with the same amounts of the same products, but the solid precipitated MNB was filtered after 5 hours of waiting and then washed, dried and analyzed for the presence of 6-MNB. The residual concentration of 2-MSB after 5 hours was at 0.06 M corresponding to more than 85% of MNB precipitation. The composition of the solid MNB samples obtained after 1 and 5 hours are presented in table 7 below.

TABLE 7

| Waiting time before filtration (min.) | 6-MNB in final MNB solid (%) |
| --- | --- |
| 60 | <0.001% |
| 300 | 0.012% |

Compared to the results presented in example 4, it may be seen that even after 5 hours of waiting period before filtration, the amount of 6-MNB is more than 140 times less (0.012% compared to 2.74% in example 4).

The aqueous phase from the selective bisulfidation step was treated in a recovery step in which the aqueous phase is treated with an alkali reagent (in this case NaOH 10%) to increase the solution pH (in this case 11) in the presence of an organic solvent in order to recover the 2-MSB adduct as 2-MNQ and minimize the losses of vitamin K3 due to the selective bisulfidation step. The experiment was carried out four times to mimic a continuous recovery step and to produce enough organic phase volume for the next step in which the obtained 2-MNQ was transformed in its bisulfite adduct. As it may be seen in table 8 below, in all the recovery experiments, the amount of 6-MNQ in the solvent was very small representing in average around 6% of the total methyl-naphthoquinones in the final organic phase.

TABLE 8

| 2-MNQ recovery experiment | 2-MSB in initial aqueous phase (M) | 6-MSB in initial aqueous phase (M) | 2-MNQ in initial solvent (M) | 6-MNQ in initial solvent (M) | 2-MNQ in final solvent (M) | 6-MNQ in final solvent (M) | MSB Extraction yield | MSB to 2-MNQ yield* |
|---|---|---|---|---|---|---|---|---|
| 1 | 0.1524 | 0.0756 | 0.0001 | <0.0001 | 0.0127 | 0.0014 | 90% | 92% |
| 2 | 0.1423 | 0.0529 | 0.0006 | <0.0001 | 0.0273 | 0.0015 | 84% | 89% |
| 3 | 0.1423 | 0.0141 | 0.0006 | <0.0001 | 0.0302 | 0.0015 | 91% | 92% |
| 4 | 0.1445 | 0.0563 | 0.0015 | 0.0004 | 0.0322 | 0.0016 | 93% | 92% |

*based on converted MSB

The organic phase from the 2-MNQ recovery experiments were then made to react with a sodium bisulfite solution to transform the 2-MNQ into its water soluble bisulfite adduct (2-MSB). The same bisulfite solution was used repeatedly to mimic a continuous bisulfidation reaction and in order to reach a high 2-MSB concentration. The amount of the bisulfite adduct of the 6 isomer (6-MSB) was at a non detectable limit (see table 9 below).

TABLE 9

| Bisulfidation cycle | 2-MNQ in initial solvent (M) | 6-MNQ in initial solvent (M) | 2-MNQ in final solvent (M) | 6-MNQ in final solvent (M) | 2-MSB (M) | 6-MSB (M) |
|---|---|---|---|---|---|---|
| 1 | 0.0127 | 0.0014 | 0.0001 | 0.0000 | 0.143 | Nd |
| 2 | 0.0290 | 0.0014 | 0.0009 | 0.0004 | 0.532 | Nd |
| 3 | 0.0320 | 0.0016 | 0.0014 | 0.0009 | 0.749 | Nd |

The obtained aqueous solution of 2-MSB was then used to produce MNB. 75 parts of the final aqueous bisulfite solution containing 0.749 M of 2-MSB and <0.0001M of 6-MSB was then used to prepare MNB by addition of an aqueous solution containing 17 parts of water and 6.8 parts of nicotinamide. 4.64 parts of sulfuric acid 93% was added gradually to the mixture over a period of 30 minutes. After a waiting period of 300 minutes, the precipitated MNB was filtered and washed with water and the solid MNB was then dried and analyzed for the presence of 6-MNB impurity. No detectable amount of 6-MNB was found in the precipitated MNB. The concentration of the residual 2-MSB reached 0.055 M corresponding to around 92% of precipitation efficiency.

EXAMPLE 6

An aqueous 0.08 M sodium bisulfite solution containing 0.1524 M of 2-MSB and 0.0284 M of 6-MSB was treated with 10% NaOH solution in the presence of an organic solvent. The final organic phase was then separated, cooled to −15° C. during 12 hours and filtered to separate the precipitated 2-MNQ solid. The experiment was repeated 4 times and the results are presented in table 10 below:

TABLE 10

| Recovery and precipitation experiment | 2-MSB initial aqueous phase (M) | 6-MSB initial aqueous phase (M) | 2-MNQ initial solvent (M) | 6-MNQ initial solvent (M) | 2-MNQ final solvent (M) | 6-MNQ final solvent (M) | 2-MNQ in solvent* | 2-MNQ precipitation yield * |
|---|---|---|---|---|---|---|---|---|
| 1 | 0.1524 | 0.0284 | 0.0019 | 0.00035 | 0.03239 | 0.00127 | 0.014743 | 54.5% |
| 2 | 0.1524 | 0.0284 | 0.0019 | 0.00035 | 0.03243 | 0.00127 | 0.014329 | 55.8% |
| 3 | 0.1524 | 0.0284 | 0.0019 | 0.00035 | 0.03401 | 0.00133 | 0.013886 | 59.2% |
| 4 | 0.1524 | 0.0284 | 0.0019 | 0.00035 | 0.03484 | 0.00121 | 0.013309 | 61.8% |

*After cooling at −15° C. during 12 hours

The average precipitation yield was around 58%. The solids obtained were combined and dried under vacuum at around 34 kPa (−20 inch Hg) in the presence of $P_2O_5$ during 72 hours. The final dry solid sowed a 2-MNQ content of more than 98.5% and less than 0.13% of 6-MNQ.

The invention claimed is:

1. A process for the production of 2-methyl-1,4-naphthoquinone and its bisulfite adducts, comprising the following steps:
   a) oxidizing 2-methyl-naphthalene (2-MNA) to achieve an organic phase containing 2-methyl-naphthoquinone (2-MNQ) and 6-methyl-naphthoquinone (6-MNQ);
   b) subjecting said organic phase to treatment with an aqueous solution of a bisulfite salt to extract preferentially the 6-MNQ isomer from the organic phase;
   c) separating said organic phase from the aqueous phase;
   d) subjecting the organic phase of process step c) to a second bisulfidation step with an aqueous solution of a bisulfite salt, resulting in an organic phase containing 2-MNA and trace amounts of 2-MNQ and an aqueous phase containing 2-MSB and trace amounts of 6-MSB;
   e) optionally removing interfering bisulfite ions from the aqueous phase of process step c);
   f) raising the pH of the aqueous phase from step c) or e) to higher than 8.5 in the presence of a solvent resulting in an organic phase containing 2-MNQ;
   g) combining the organic phase from step f) with the organic phase being treated in the process step d);
   h) recycling the organic phase from step d) back to step a) to be used as solvent for the oxidation reaction of 2-MNA.

2. The process according to claim 1, wherein the organic phase from step c) is used to produce pure solid 2-MNQ by cooling and by separating the precipitated 2-MNQ by any known solid-liquid separation method before being subjected to the second bisulfidation in step d).

3. The process according to claim 1, wherein said aqueous phase from process step d) is isolated and the bisulfite adduct of the 2 isomer is precipitated and isolated or used as a reactant to prepare other Vitamin K3 derivatives.

4. Process according to claim 1, wherein the step e) for the removal of interfering bisulfite ions is effected by a method selected from the group consisting of selective precipitation, ion exchange treatment, membrane treatment or conversion into inert ions.

5. The process according to claim 1, wherein process step f) is performed in the absence of an organic solvent and the 2-MNQ is isolated as a precipitated solid by any solid-liquid separation method.

6. The process according to claim 1, wherein process step a) takes place at a temperature in the range of 0-100° C.

7. The process according to claim 1, wherein process step a) employs an oxidizing agent selected from the group consisting of a Ce(III)/Ce(IV) salt redox couple.

8. The process according to claim 7, wherein the spent cerium salt is re-oxidized by using an electrochemical cell.

9. The process according to claim 1, wherein process step b) as well as process step d) are carried out at a temperature in the range of 0-70° C.

10. The process according to claim 1, wherein process step b) as well as process step d) use a solution containing a bisulfite salt, selected from the group consisting of sodium or potassium bisulfite.

11. The process according to claim 1, wherein said bisulfite solution in process step b) has a concentration of 0.1-4 M.

12. The process according to claim 6, wherein process step a) takes place at a temperature in the range of 25-60° C.

13. The process according to claim 12, wherein process step a) takes place at a temperature in the range of 25-40° C.

14. The process according to claim 9, wherein process step b) as well as process step d) are carried out at a temperature in the range of 10-50° C.

15. The process according to claim 14, wherein process step b) as well as process step d) are carried out at a temperature in the range of 25-40° C.

16. The process according to claim 11, wherein said bisulfite solution in process step b) has a concentration of 0.5-2 M.

17. The process according to claim 16, wherein said bisulfite solution in process step b) has a concentration of 0.5 M.

* * * * *